United States Patent [19]

Worsham et al.

[11] 4,226,740

[45] Oct. 7, 1980

[54] INFRA-RED RESPONSIVE FINGERPRINT COMPOSITION AND METHOD OF MAKING

[75] Inventors: Robert Worsham, Opa Locka; Kurt L. Jenkins, Miami, both of Fla.

[73] Assignee: Criminalistics, Inc., Miami, Fla.

[21] Appl. No.: 10,736

[22] Filed: Feb. 9, 1979

[51] Int. Cl.$^3$ .................... A61B 5/10; C09K 3/00
[52] U.S. Cl. ..................... 252/408; 106/19; 106/21; 106/129; 252/301.4 R; 427/1; 427/145
[58] Field of Search ............. 252/408, 301.4 R, 182; 106/19, 21, 129; 430/465, 477; 427/1, 145; 118/31.5

[56] References Cited

U.S. PATENT DOCUMENTS

| | | | |
|---|---|---|---|
| 1,259,981 | 3/1918 | Hedrick | 427/1 |
| 1,539,448 | 5/1925 | White | 118/31.5 |
| 1,667,542 | 4/1928 | Flanagan | 118/31.5 |
| 1,951,203 | 3/1934 | Pitman | 427/1 |
| 2,299,652 | 10/1942 | Rahn | 118/31.5 |
| 2,447,322 | 8/1948 | Fonda | 252/301.4 R |
| 2,986,831 | 6/1961 | Terek et al. | 427/1 |
| 3,075,852 | 1/1963 | Bonora | 427/1 |
| 3,132,036 | 5/1964 | MacDonell | 118/31.5 |
| 4,176,205 | 11/1979 | Molina | 427/1 |
| 4,182,261 | 1/1980 | Smith et al. | 118/31.5 |

*Primary Examiner*—Teddy S. Gron
*Attorney, Agent, or Firm*—O'Brien & Marks

[57] ABSTRACT

An infra-red responsive fingerprint composition and method for manufacturing by sifting and mixing a minor proportion of finely divided carbon black (50 to 75 millimicrons) and a major proportion of infra-red responsive finely divided pigments containing milori blue (250 to 400 mesh), manganese dioxide (300 to 400 mesh), aluminum powder (1 to 75 microns) and mica (10 to 20 microns). A small amount of gum arabic as binder is included to facilitate adhesion of the print powder to latent prints. On white surfaces the fingerprint powder is black. On dark surfaces the fingerprint powder is brightly reflective so that when lifted or transferred to a white backing the color changes from brightly reflective to black. The reflective color becomes even more vivid under infra-red. Storage is preferably in tightly sealed containers in the presence of dessicant capsules to prevent moisture pick-up and caking of the gum arabic.

4 Claims, No Drawings

INFRA-RED RESPONSIVE FINGERPRINT COMPOSITION AND METHOD OF MAKING

BACKGROUND OF THE INVENTION

1. Field of the Invention

The invention relates to a novel fingerprint powder usable in the customary manner by sprinkling on latent prints, brushing off surplus and taking an impression by means of a tape, as well as by photographing. The invention further relates to methods of mixing the novel powder composition and to storing the composition under conditions where it can be used as affectively at a later time as when freshly made.

2. Description of the Prior Art

In Hedrick, U.S. Pat. No. 1,259,981, the standard black fingerprint powder is described as a combination of lamp black and gum adhesive and the use of the powder for taking prints is also taught employing the technique of spraying the print after dusting with an alcohol solvent to dissolve the gum.

In White, U.S. Pat. No. 1,539,448, the use of a variety of differently colored print powders, each in its own container, is taught as an improvement for detecting latent prints left on a variety of surfaces.

In Pitman, U.S. Pat. No. 1,951,203, the use of aluminum powder as a highly reflective component of the powder is disclosed.

In Fonda, U.S. Pat. No. 2,447,322, iron compounds are disclosed at column 2, line 5, as storage agents to retard the exhaustion of infra-red luminescence. At column 2, lines 35 et seq., manganese compounds are disclosed as activating agents for such storage.

In Terek, U.S. Pat. No. 2,986,831, print powders based on lamp black or aluminum are used to make transfer prints or photographs.

Similarly, in Bonora, U.S. Pat. No. 3,075,852, either carbon black or aluminum powder is used to make prints.

Each of the above black fingerprint powders has the disadvantage of requiring a cumbersome variety of mixtures in containers and applicators and of further requiring a high degree of skill is using these multiple containers and applicators.

OBJECTS OF THE INVENTION

It is a primary object of the invention to provide a single fingerprint powder composition to replace the conventional carbon black pigment or aluminum pigment powders which is brighter and displays much higher contrast under reflected visible light and is further intensified in brightness and contrast under infra-red radiation to thereby improve the art of fingerprinting.

It is a further object of the invention to provide improved fingerprint detection and recording by transfer and by photographing, under infra-red light, the print developed by dusting with the new fingerprint powder of the invention.

SUMMARY OF THE INVENTION

To accomplish the above objects, the novel fingerprint powder composition of the invention uses a combination of finely divided infra-red responsive pigments and visible light reflective pigments, the infra-red pigments including manganese dioxide and milori blue while the visible light reflective pigments include carbon black, mica and aluminum powders. A small but effective amount of adhesive, such as gum arabic, is added as a binder. Thorough mixing and sifting of the finely divided powders is carried out under by conditions and the thoroughly mixed product is stored in the presence of dessicant capsules to assure that caking will not occur during prolonged storage.

Proportions, as identified blow, are critical:

| Ingredient | Range of Particle Size | Preferred Proportions | Range of Proportions By Weight |
|---|---|---|---|
| Aluminum | 1-75 microns | 17% | 6-20% |
| Carbon Black | 5-70 millimicrons | 36% | 30-48% |
| Manganese Dioxide | 300-400 mesh | 18% | 6-18% |
| Milori Blue | 250-400 mesh | 15% | 6-18% |
| Mica | 10-20 microns | 12% | 6-18% |
| Gum Arabic | USP Grade | 3% | 2-9% |

The particle size of each of the finely divided pigments set forth above is critical in order to achieve proper mixing in the dry state and to overcome the well known problems associated with carbon black fingerprint powders. The particle size of carbon black fingerprint powders using only gum arabic binder requires a very delicate balance between the properties of binder and carbon black which interferes with the use of the powder if it takes up moisture or is used under humid conditions. The black agglomerates and indistinct prints results because particles do not easily brush away. With the invention, all of the beneficial properties of the cabon black are retained with none of the faults mentioned above because each of manganese dioxide, milori blue, aluminum and mica is non-hygroscopic, non-agglomerating, highly reflective and intensely colored with separate spectral characteristics under visible and infra-red light.

A unique coaction has been discovered between these aforementioned, non-carbon pigments, the gum binder and the carbon black to retain the print transfer capability of carbon black while adding unexpected characteristics of spectral reflectants to vividly outline latent prints based upon the non-carbon pigments. Manganese dioxide, an oxidizing agent, has a surprising effect on the enhancement of the print color under infra-red light which is unexpected. It is a stable, black tetravalent oxide of high hardness (6-6.5 Mohs scale) and high specific gravity (5.06) and would be expected to have no enhancement on infra-red phosphorescence or luminescence, when used in combination with milori blue. Milori blue is not used in phosphor compositions. Where manganese compounds have been used, as in Homer, U.S. Pat. No. 2,647,086, the compound is manganese carbonate used with cadmium phosphors and calcium phosphors. These are phorphors adversely affected by oxidation and obviously not suitable if the manganese carbonate was interchanged with manganese dioxide, an oxidizing agent.

Milori blue is described at page 600, under iron blue, and at page 730, under milori blue, of Condensed Chemical Dictionary, Fifth Edition, Reinhold Publishing Company, 1956, as a commercial blue pigment having very dark intense mass tones and a green tint made by reacting a soluble ferrocyanide salt with iron sulphate thereby forming a ferrous ferrocyanide which is then oxidized to a ferric ferrocyanide. Kirk-Othmer, *Encyclopedia of Chemical Technology*, Second Edition, defines milori blue as a mixture of the ferric and ferrous salts which have the darkest and most intense tones of all of the manufactured blues and a characteristic green tint. It is the discovery of the properties of the black pigment effect of manganese dioxide and the green tint effect of milori blue that creates the new reflective results under visible and infra-red lights for the composition of the invention.

Reflective aluminum and reflective mica introduce specular reflection into the mixture and contribute to the intensification of the visual or photographic image of the print. Thus, these function as miniature light reflectors.

DESCRIPTION OF THE PREFERRED EMBODIMENT

The following examples illustrate preferred compositions of the invention for use on differently colored surfaces:

EXAMPLE 1

Aluminum powder of 16 micron particle size was obtained as powder, grade number 1400, from Gold Leaf and Metallic Powders, Inc., Two Barclay Street, New York, New York 10017 and was mixed in an amount of 17 ounces with 36 ounces of carbon black, particle size 75 millimicons, in a five gallon drum, each of the two ingredients being passed through a sifter while being stirred by hand with a wooden spatula. This two component mixture was black in color despite the silvery appearance of the aluminum powder. To this mixture was added 18 ounces of 400 mesh manganese dioxide, technical grade, purchased from J. T. Baker Chemical Company, 222 Red School Lane, Phillipsburg, New Jersey 08865, 12 ounces of 10 to 20 micron powdered mica, purchased from English Mica Company, Kings Mountain, North Carolina, under grade number Micro-Mica 1000 and 15 ounces of 325 mesh milori blue, purchased from Mineral Pigments Corporation, 7011 Muirkirk Road, Beltsville, Maryland 20705. During the addition of the black manganese dioxide, milori blue and mica pigments there was simultaneously mixed 3 ounces of USP gum arabic which was in finely divided condition from the supplier, Amend Drug and Chemical Company, Irvington, New Jersey 07111.

After hand mixing for three to five minutes the drum was sealed, placed on a rotary mixer and mixed for an additional hour. The drum was then opened, inspected, hand-turned with the wooden spatula to verify mixing and then run through a sifter to remove any agglomerated particles.

The sifted mixture was then stored with 1 to 2 dessicant capsules (anhydrous pressed silicon gel) in sealed 2, 4 and 8 ounce double-walled containers.

EXAMPLE 2

The same mixing procedure and the same proportions as in Example 1 were followed except that the amount of milori blue was changed from 15 ounces to 18 ounces and the amount of manganese dioxide was changed from 18 ounces to 15 ounces.

The product worked equally well as that of Example 1.

EXAMPLE 3

The same mixing procedure and same proportions were followed as in Example 1 except that the amount of carbon black was reduced to 33 ounces instead of 36 ounces and the amount of milori blue was increased from 15 ounces to 18 ounces.

This product also worked equally well as that of Example 1.

In each of the above examples, each ounce corresponds to about 1% by weight of the composition.

Although each of the above examples provides excellent results which are far superior than those using the straight carbon black or multi-colored sets of finger prints powders, it is possible to vary, for each ingredient, the proportions as set forth under the Summary of the Invention.

If aluminum is reduced to less than 6% by weight, the specular reflective benefit of aluminum is lost and the disadvantage of carbon black takes over. Although carbon black may be increased up to 48%, it is preferred that it represent about one-third of the composition. Less than 30% of carbon black results in a loss of contrast for print development.

If manganese dioxide is used at a level less than 6%, the improvement of the surplus dust removal effect for the composition is lost. The optimum proportion at about 14 to 18% gives best balance for removal of surplus dust.

If milori blue is used at less than 6%, the desirable green tint and the combined effect with manganese dioxide under infra-red is lost. The best color balance is between 15 to 18% for each of milori blue and manganese dioxide.

Mica provides an entirely different effect than aluminum due to its lubricating properties and also due to a different type of reflection which is effective at greater than 6%.

Gum arabic is preferably used at a minimum level, e.g., 2 to 3%. Larger amounts are less preferred because it adversely affects storage. More than 9% cannot be used.

Having thus disclosed the invention, we now claim:

1. A fingerprint composition for use under ordinary light and under infra-red consisting essentially of a mixture of the following finely divided powders:
   aluminum in a particle range of 1 to 75 microns and a proportion of 6% to 20% by weight;
   carbon black in a particle range of 5 to 70 millimicrons and a proportion of 30% to 48% by weight;
   manganese dioxide in a particle range of 300 to 400 mesh and a proportion of 6% to 18% by weight;
   milori blue in a particle range of 250 to 400 mesh and a proportion of 6% to 18% by weight;
   mica in a particle range of 10 to 20 microns and a proportion of 6% to 18% by weight; and
   gum arabic as a binder in a proportion of 2% to 9% by weight.

2. A fingerprint composition as claimed in claim 1 wherein the proportion of gum arabic is 2% to 3%.

3. A fingerprint composition as claimed in claim 1 wherein the proportion of aluminum is 17% and its particle size is about 16 microns, the proportion of carbon black is 36% and its particle size is about 75 millimicrons, the proportion of mica is 12% and its particle size is about 10 to 20 microns, the proportion of manganese dioxide is 18% and its particle size is 400 mesh, and the proportion of milori blue is 15% and its particle size is 325 mesh.

4. A method of mixing and thereafter storing an infra-red light responsive fingerprint composition comprising first adding, sifting and mixing aluminum powder in a particle range of 1 to 75 microns and a proportion of 6% to 20% by weight and carbon black in a particle range of 5 to 70 millimicrons and a proportion of 30% to 48% by weight;

then adding to the above mixture manganese dioxide in a particle range of 300 to 400 mesh and a proportion of 6% to 18% by weight, milori blue in a particle range of about 250 to 400 mesh and a proportion of 6% to 18% by weight, mica in a particle range of 10 to 20 microns and a proportion of 6% to 18% by weight and finely divided gum arabic, as binder, in a proportion of 2% to 9% by weight;

thoroughly mixing the above mixture by hand;

sifting the mixture to remove lumps;

mixing on a rotary mixer for about one-half hour to one hour; and storing the mixture in the presence of dessicant capsules in a tightly sealed container.

* * * * *